United States Patent
McMichael et al.

(10) Patent No.: US 11,944,761 B2
(45) Date of Patent: *Apr. 2, 2024

(54) SYSTEM AND METHOD FOR MEDICAL DEVICE POSITION GUIDANCE

(71) Applicant: Avent, Inc., Alpharetta, GA (US)

(72) Inventors: Donald McMichael, Roswell, GA (US); Shawn G. Purnell, Sandy Springs, GA (US)

(73) Assignee: Avent, Inc., Alpharetta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/665,686

(22) Filed: Feb. 7, 2022

(65) Prior Publication Data
US 2022/0226609 A1    Jul. 21, 2022

Related U.S. Application Data

(63) Continuation of application No. 16/377,329, filed on Apr. 8, 2019, now Pat. No. 11,273,288.

(51) Int. Cl.
| | |
|---|---|
| *A61B 5/05* | (2021.01) |
| *A61B 34/20* | (2016.01) |
| *A61B 90/00* | (2016.01) |
| *A61J 15/00* | (2006.01) |
| *A61M 25/01* | (2006.01) |

(52) U.S. Cl.
CPC ......... *A61M 25/0127* (2013.01); *A61B 34/20* (2016.02); *A61B 90/37* (2016.02); *A61J 15/0003* (2013.01); *A61J 15/0088* (2015.05); *A61B 2034/2051* (2016.02); *A61B 2090/367* (2016.02)

(58) Field of Classification Search
CPC .... A61M 25/0127; A61B 34/20; A61B 90/37; A61B 2034/2051
See application file for complete search history.

(56) References Cited

U.S. PATENT DOCUMENTS

| 4,836,214 A | 6/1989 | Sramek |
|---|---|---|
| 4,921,481 A | 5/1990 | Danis et al. |
| 6,334,064 B1 | 12/2001 | Fiddian-Green |
| 6,357,447 B1 | 3/2002 | Swanson et al. |

(Continued)

FOREIGN PATENT DOCUMENTS

| EP | 1 837 828 A2 | 9/2007 |
|---|---|---|
| WO | WO 92/17150 | 10/1992 |

(Continued)

OTHER PUBLICATIONS

International Search Report and Written Opinion for PCT/US2020/026872, dated Jun. 26, 2020, 16 pages.

*Primary Examiner* — Joel F Brutus
(74) *Attorney, Agent, or Firm* — Dority & Manning, P.A.

(57) ABSTRACT

A medical device position guidance system includes a plurality of noninvasive external detector devices communicable with an invasive medical device. A magnetic field is used to gather information about the anatomical size and shape of a subject, such as a human. The medical device position guidance system further uses the magnetic field to obtain information about the positioning of the invasive medical device relative to the subject's anatomy. A method of using the medical device position guidance system is also provided.

20 Claims, 7 Drawing Sheets

(56) References Cited

U.S. PATENT DOCUMENTS

| | | |
|---|---|---|
| 7,818,155 B2 | 10/2010 | Stuebe et al. |
| 8,147,486 B2 | 4/2012 | Honour et al. |
| 8,613,702 B2 | 12/2013 | Feer et al. |
| 8,801,601 B2 | 8/2014 | Prisco et al. |
| 8,986,230 B2 | 3/2015 | Nishtala |
| 9,179,971 B2 | 11/2015 | Kirschenman |
| 9,226,878 B2 | 1/2016 | Elia et al. |
| 9,295,395 B2 | 3/2016 | Elia et al. |
| 9,532,739 B2 | 1/2017 | Bennett-Guerrero |
| 9,610,227 B2 | 4/2017 | Elia |
| 9,642,779 B2 | 5/2017 | Elia et al. |
| 9,713,579 B2 | 7/2017 | Elia et al. |
| 9,918,907 B2 | 3/2018 | Kuhn |
| 2008/0097179 A1 | 4/2008 | Russo |
| 2008/0167607 A1 | 7/2008 | Pfeiffer et al. |
| 2008/0249467 A1 | 10/2008 | Burnett et al. |
| 2008/0319349 A1* | 12/2008 | Zilberman ............ A61B 5/0031 600/587 |
| 2011/0034798 A1 | 2/2011 | Payner |
| 2012/0016256 A1 | 1/2012 | Mabary et al. |
| 2012/0277619 A1 | 11/2012 | Starkebaum et al. |
| 2013/0144124 A1 | 6/2013 | Prisco et al. |
| 2013/0197357 A1 | 8/2013 | Green et al. |
| 2013/0225946 A1 | 8/2013 | Feer et al. |
| 2014/0357984 A1 | 12/2014 | Wallace et al. |
| 2015/0196229 A1 | 7/2015 | Old et al. |
| 2015/0238388 A1 | 8/2015 | Kuhn |
| 2015/0282734 A1 | 10/2015 | Schweikert et al. |
| 2016/0113843 A1 | 4/2016 | Elia et al. |
| 2016/0129223 A1 | 5/2016 | Kirschenman |
| 2016/0331298 A1 | 11/2016 | Burnett et al. |
| 2017/0071502 A1 | 3/2017 | Bennett-Guerrero |
| 2017/0119329 A1 | 5/2017 | Warner et al. |
| 2017/0202750 A1 | 7/2017 | Elia |
| 2018/0049810 A1* | 2/2018 | Besser .................. A61B 5/743 |
| 2018/0078195 A1 | 3/2018 | Sutaria et al. |
| 2018/0092698 A1* | 4/2018 | Chopra .................. A61B 90/39 |
| 2018/0110440 A1 | 4/2018 | Tegg |
| 2018/0161249 A1 | 6/2018 | Elia et al. |
| 2018/0289536 A1 | 10/2018 | Burnett |
| 2019/0101415 A1 | 4/2019 | Sekeljic et al. |

FOREIGN PATENT DOCUMENTS

| | | |
|---|---|---|
| WO | WO 2006/076214 A2 | 7/2006 |
| WO | WO 2016/005983 A2 | 1/2016 |

\* cited by examiner

SYSTEM AND METHOD FOR MEDICAL DEVICE POSITION GUIDANCE

RELATED APPLICATIONS

This application is a continuation of U.S. application Ser. No. 16/377,329, filed on Apr. 8, 2019, the entirety of which is hereby incorporated by reference for all purposes.

FIELD OF THE INVENTION

The subject matter of the present invention relates generally to a medical device position guidance system and method.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These intravascular catheters include, among others, central venous catheters, peripheral venous catheters and the peripherally inserted central catheters. These catheters include a relatively small tube that passes through the patient's veins or arteries. Depending on the application, the health care provider can use an intravascular catheter to remove blood vessel blockages, place inserts into blood vessels and provide patients with injections of medications, drugs, fluids, nutrients, or blood products over a period of time, sometimes several weeks or more.

When using these known enteral and intravascular catheters, it is important to place the end of the catheter at the proper location within the human body. Erroneous placement of the catheter tip may injure or harm the patient. For example, if the health care provider erroneously places an enteral catheter into the patient's lungs, liquid may be introduced into the lungs with harmful results. If the health care provider erroneously places an intravascular catheter into the wrong blood vessel of the cardiovascular system, the patient may experience infection, injury or a harmful blockage.

With feeding tubes in particular, it is also prudent to check that the exit aperture of the feeding tube (typically located at the distal end/tip of the tube) remains in its desired location over the period of treatment, e.g., feeding. Protocols that address this requirement in enteral feeding tubes include frequent monitoring for the appropriate pH of fluids extracted from the feeding tube when not carrying nutritional liquids and careful patient monitoring to ensure nutritional uptake is as expected.

In some cases, health care providers use X-ray machines to gather information about the location of catheters within the body. There are several disadvantages with using X-ray machines. For example, these machines are relatively large and heavy, consume a relatively large amount of energy and expose the patient to a relatively high degree of X-ray radiation. Also, these machines are typically not readily accessible for use because, due to their size, they are usually installed in a special X-ray room. This room can be far away from the patient's room. Therefore, health care providers can find it inconvenient to use these machines for performing catheter insertion procedures. Furthermore, it can be inconvenient to transport these machines to a patient's home for home care catheter procedures. Moreover, even X-rays are not necessarily conclusive as to the location of the catheter tip, as the natural and continuous movement of the internal organs can make it difficult for the physician interpreting the X-ray to be sure of the actual location of the distal end of the catheter.

Another existing catheter locating means involves using an electromagnetic coil positioned inside the catheter and an electromagnetic coil locating receiver outside of the patient's body. The electromagnetic coil is generally incorporated into a stylet or guide wire which is inserted within the catheter. The coil locating receiver can be used to determine the distance the coil is from the receiver and its depth in the patient's body and can communicate with a display to show a reference image of a non-subject body and an image of the coil located on the display with the reference image. However, these systems also have several disadvantages. For example, the coil locating receiver is a large device that must rest in a precise location outside the patient's body and does not permit for adjustments due to each individual patient's anatomical size or shape. However, a patient undergoing a feeding tube placement will be agitated and sudden movements are expected, which can move the coil locating receiver, thus increasing the likelihood of positional errors or complications in locating the catheter. Additionally, these existing systems can only display the coil location over a reference image of a non-subject (i.e., a generic patient) body without reference to the individual patient's particular anatomy. Therefore, health care providers can estimate the positioning of the catheter using the electromagnetic coil and coil locating receiver but cannot estimate or view the specific patient's anatomy.

Consequently, there is a need for a medical device, e.g., catheter, position guidance system that is adaptable to patients of all sizes to ensure more accurate catheter placement. In particular, a medical device position guidance system that provides a stationary frame of reference with the patient and determines patient anatomical shape and size would also be useful.

SUMMARY

The present invention is directed to a medical device position guidance system. The system includes a processor, a plurality of external detector devices, a display device, and a memory device. The plurality of external detector devices are configured to be positioned in a predetermined external arrangement on a subject. Each detector device is operatively coupled to the processor. Each of the plurality of external detector devices are configured to interrogate each other to determine a distance between each of the plurality of detector devices. The memory device stores instructions which when executed by the processor, cause the processor to: (i) receive signals relating to the distance between each of the plurality of detector devices from each of the plurality of detector devices to determine a three-dimensional volume between the plurality of external detector devices; (ii) using the received data from the plurality of external detector devices and the three-dimensional volume to determine an anatomical shape, size, and/or orientation of the subject within the three-dimensional volume; and (iii) cause the display device to display the anatomical shape, size, and/or orientation of the subject within the three-dimensional volume.

In one particular embodiment, the plurality of external detector devices includes a first external detector device, a second external detector device, and a third external detector device. Moreover, the predetermined external arrangement can be based on at least one bony landmark of the subject. Further, the predetermined external arrangement can include the first external detector device configured to be placed on a right upper landmark of the subject, the second external detector device configured to be placed on a left upper landmark of the subject, and the third external detector device configured to be placed on a central landmark of the subject. In addition, the system can be configured to maintain a stationary frame of reference relative to the subject.

In another embodiment, the determined anatomical shape and size of the subject comprises an external anatomical shape and size of the subject. Moreover, the memory device can further include information defining a pre-defined anthropometric relationship between the external anatomical shape and size of the subject and the internal anatomical shape and size of the subject, further wherein the display can be configured to display the internal anatomical shape and size of the subject within the three-dimensional volume. Further, the internal anatomical shape and size of the subject within the three-dimensional volume can include internal organs within the three-dimensional volume displayed in approximate size and location within the three-dimensional volume.

In an additional embodiment, the system can further include a medical device configured to be placed within the subject, wherein the medical device includes an electromagnetic sensor configured to be placed within the subject. The processor can be configured to: (i) determine a distance between the electromagnetic sensor and each of the plurality of external detector devices; and (ii) cause the display device to display a position of the electromagnetic sensor in relation to the anatomical shape, size, and/or orientation of the subject within the three-dimensional volume.

In a further embodiment, each of the plurality of external detector devices can include a housing that is configured to be affixed to the subject. Moreover, the housing of each of the plurality of external detector devices can be configured to be adhesively affixed to the subject.

In yet another embodiment, each of the plurality of external detector devices can further include a wireless communication device configured to communicate wirelessly with the processor.

In still another embodiment, each of the plurality of external detector can be configured to communicate with the processor via a wired connection.

In one more embodiment, each of the plurality of external detector devices can include an electromagnetic emitter and/or an electromagnetic receiver.

The present invention is further directed to a method of noninvasively determining a size and shape of a subject. The method includes steps of: placing a plurality of external detector devices in a predetermined external arrangement on the external anatomy of the subject; measuring a distance between each of the plurality of external detector devices to determine a three-dimensional volume; determining an anatomical shape and size of the subject within the three-dimensional volume; and displaying the anatomical shape and size of the subject within the three-dimensional volume on a display device.

In one particular embodiment, the plurality of external detector devices can include a first external detector device, a second external detector device, and a third external detector device, and the step of measuring can include the first external detector device, the second external detector device, and the third external detector device interrogating each other to triangulate the three-dimensional volume.

Moreover, the predetermined external arrangement can include the first external detector device placed on a right upper landmark of the subject, the second external detector device placed on a left upper landmark of the subject, and the third external detector device placed on a central landmark of the subject.

Further, the step of displaying the anatomical shape and size of the subject can include displaying the shape of at least one internal organ in approximate size and location within the three-dimensional volume.

In another embodiment, the method can further include steps of: inserting a feeding tube into the subject, wherein the feeding tube includes an electromagnetic sensor in an insertion end of the feeding tube; determining a distance between the electromagnetic sensor and each of the plurality of external detector devices; and displaying a position of the electromagnetic sensor in relation to the anatomical shape and size of the subject within the three-dimensional volume on the display device.

In an additional embodiment, each of the plurality of external detector devices can include an electromagnetic emitter and/or an electromagnetic receiver.

In one more embodiment, the step of placing a plurality of external detector devices in a predetermined external arrangement on the subject includes affixing each of the plurality of external detector devices to the subject. Moreover, the external detector devices affixed to the subject can maintain a stationary frame of reference relative to the subject.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1A:
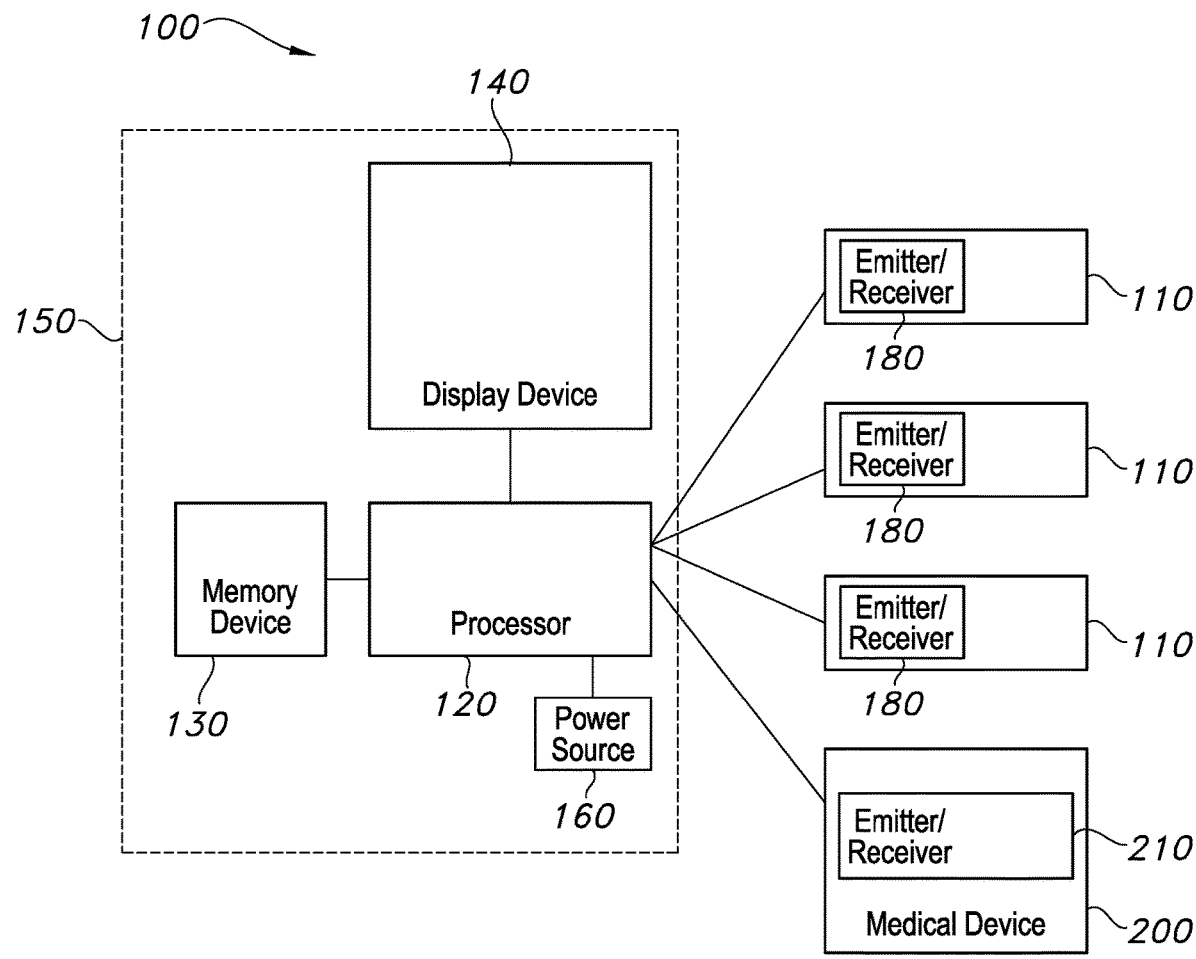
FIG. 1A illustrates a block diagram of a medical device position guidance system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

Generally speaking, the present invention is directed to a medical device position guidance system. The medical device position guidance system includes a plurality of external detector devices configured to be positioned in a predetermined external arrangement on a subject. The system additionally includes a processor, and each detector device is operatively coupled to the processor. Each of the plurality of external detector devices are configured to interrogate each other to determine a distance between each of the plurality of detector devices. The system further includes a display device and a memory device. The memory device stores instructions which when executed by the processor, cause the processor to: (i) receive signals relating to the distance between each of the plurality of detector devices from each of the plurality of detector devices to determine a three-dimensional volume between the plurality of external detector devices; (ii) using the received data from the plurality of external detector devices and the three-dimensional volume to determine an anatomical shape, size, and/or orientation of the subject within the three-dimensional volume; and (iii) cause the display device to display the anatomical shape, size, and/or orientation of the subject within the three-dimensional volume. The present invention is also directed to a method of determining the size and shape of a subject using the medical device position guidance system. Because of the specific components of the medical device position guidance system, the present inventors have found that the patient's anatomical shape and size can be more accurately determined and represented for use in the insertion of an invasive medical device into the patient's body due to the stationary frame of reference of the external devices relative to the patient. Moreover, the present inventors have found that the medical device position guidance system of the present invention can reduce complications that can arise due to positional errors resulting from the movement of a patient during use of the medical device position guidance system.

The specific features of the medical device position guidance system of the present invention may be better understood with reference to FIGS. 1A-7.

Referring now to the drawings, FIG. 1A illustrates one embodiment of a medical device position guidance system 100. The medical device position guidance system 100 includes (a) an apparatus 150 having a housing which supports a controller or processor 120 and a display device 140; (b) a plurality of non-invasive external detector devices 110 electronically coupled to the processor by a wire, cable, signal data connection, signal carrier or wireless connection; (c) a power source 160 coupled to the apparatus 150; and optionally (d) an invasive medical device 200 in communication with the plurality of external detector devices 110 and operatively coupled to the apparatus 150 by a wire, cable, cord or electrical extension, which, in turn, is operatively coupled to the processor 120. Each of the plurality of external detector devices 110 are configured to be positioned in a distributed arrangement on a surface of a subject 10 (see FIG. 2) which is a mammal, such as a human. Although the illustrated example depicts a human, it should be appreciated that medical device position guidance system 100 could be used with any mammals such as domestic animals. In general, and referring to FIGS. 1A-B and 4, the plurality of noninvasive external detector devices 110 each includes a housing 112 which supports an electromagnetic field emitter/receiver 180 operably coupled to the processor 120, where the processor 120 is coupled to a memory device 130. According to the embodiment, the medical device position guidance system 100 is operable to provide audiovisual information about the shape, size, and orientation of a subject's anatomy through a wired or wireless connection between the plurality of external detector devices 110 and a computer 150 having a processor 120 and a display device 140. The medical device position guidance system 100 can be further operable to provide audiovisual information about the position and orientation of the invasive medical device 200 relative to the plurality of external detector devices 110 and the patient's detected anatomy, through a wired or wireless connection between the plurality of external detector devices 110, the invasive medical device 200, and the computer 150 having a processor 120 and a display device 140.

Figure 4:
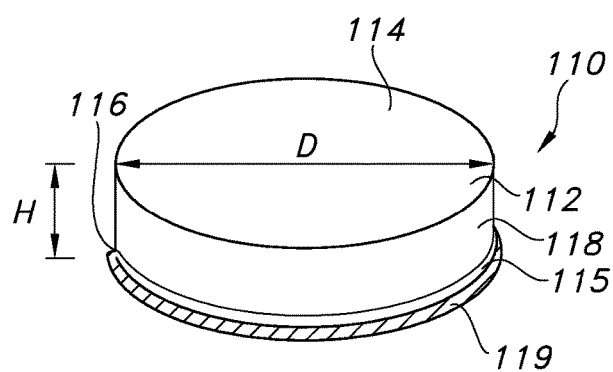
FIG. 4 illustrates a perspective view of a housing of an external detector device of the medical device position guidance system of the present invention.

As illustrated in FIGS. 1A, 2 and 4-5, each of the external detector devices 110 includes a housing 112 surrounding an electromagnetic emitter and/or receiver 180. The housing 112 can include an upper surface 114, a lower surface 116, and at least one side surface 118 extending from the upper surface to the lower surface. For example, as shown in FIG. 4, the upper surface 114 and the lower surface 116 can be circular or oval in shape and have a continuous side surface 118 extending therebetween, forming a generally cylindrical-shaped housing 112. In another embodiment (not shown), the upper surface 114 and the lower surface 116 can be rectangular in shape and can have four side surfaces 118 extending therebetween corresponding to each of the sides of the rectangle. However, the external shape of the housing 112 of each external detector device 110 is of little consequence to the way in which the actual electromagnetic emitter and/or receiver 180 works. As such, the housing 112 can have any other suitable external shape based on a particular application of the medical device position guidance system 100.

The housing 112 of each external detector device 110 can have a footprint (i.e., shape and size of the lower surface 116) that is generally comparable to standard electrocardiogram leads. For example, the housing 112 can have a diameter D extending across the widest portion of the upper surface 114 or lower surface 116 that is in a range from about 0.5 inches (1.25 cm) to about 5 inches (13 cm), or any value or range therebetween, such as from about 1 inch (2.5 cm) to about 3 inches (7.6 cm), for example from about 1.5 inches (3.8 cm) to about 2.5 inches (6.4 cm). The at least one side surface 118 of the housing 112 can have a height H in a range from about 0.25 inches (0.63 cm) to about 2 inches (5.1 cm), or any value or range therebetween, such as from 0.3 inches (0.76 cm) to about 1 inch (2.5 cm), for example about 0.5 inches (1.25 cm). In addition, each of the external detector devices 110 can be lightweight.

Figure 5A:
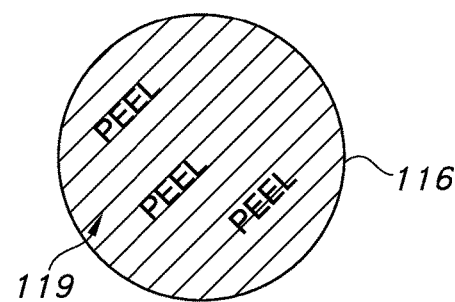
FIGS. 5A-B illustrate bottom views of the housing of FIG. 4.
Figure 5B:
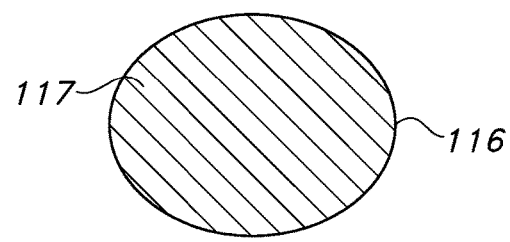

As shown in FIGS. 4 and 5A-B, each external detector device 110 can further include a fixation mechanism 115 that is configured to affix the external detector device 110 to the subject. In a preferred embodiment, the external detector device 110 can be directly affixed to the subject's body 10 by the fixation mechanism 115 so that the external detector device 110 maintains a fixed reference point in relation to the subject 10. Thus, when the subject 10 moves, the external detector device 110 moves with the subject 10 to maintain a static frame of reference with respect to the particular patient. The fixation mechanism 115 can be positioned on the lower surface 116 of the external detector device housing 112. For example, the fixation mechanism 115 can include an adhesive material 117 that is configured to affix the external detector device 110 to the skin of the subject, a patch on the subject's body, or a garment worn by the subject. The adhesive material 117 can be an adhesive substrate that can be adhesive on both sides such that it adheres to the lower surface 116 of the housing 112 on one side and to a subject's body or garment on the other side. When the fixation mechanism 115 is adhesive material 117 adhered to the lower surface 118 of the housing 112, the external detector device 110 can additionally include a peelable protective sheet 119 covering the entire adhesive material 117. The peelable protective sheet 119 can be removed prior to affixing the adhesive 117 to the subject 10 or the subject's garment. Optionally, a used adhesive substrate 117 can be removed from the housing 112 and discarded, and a new adhesive substrate 117 can be applied. Alternatively, the adhesive material 117 can be any suitable adhesive arrangement which is capable of releasably adhering the housing 112 to the subject's skin or garment. In other embodiments, the fixation mechanism 115 can include a clip, pin, magnet, hook and loop system, or any other suitable means for affixing the external detector device 110 to a subject's body or garment. By using a fixation mechanism 115 on each external detector device 110 that can affix the external detector device 110 to the subject's body or garment, the frame of reference of each external detector device 110 can remain stationary with the subject's body. Thus, the likelihood of positional errors when using the medical device position guidance system 100 can be reduced as compared to other guidance systems because there can be fewer complications arising due to movement of the subject's body.

Figure 2:
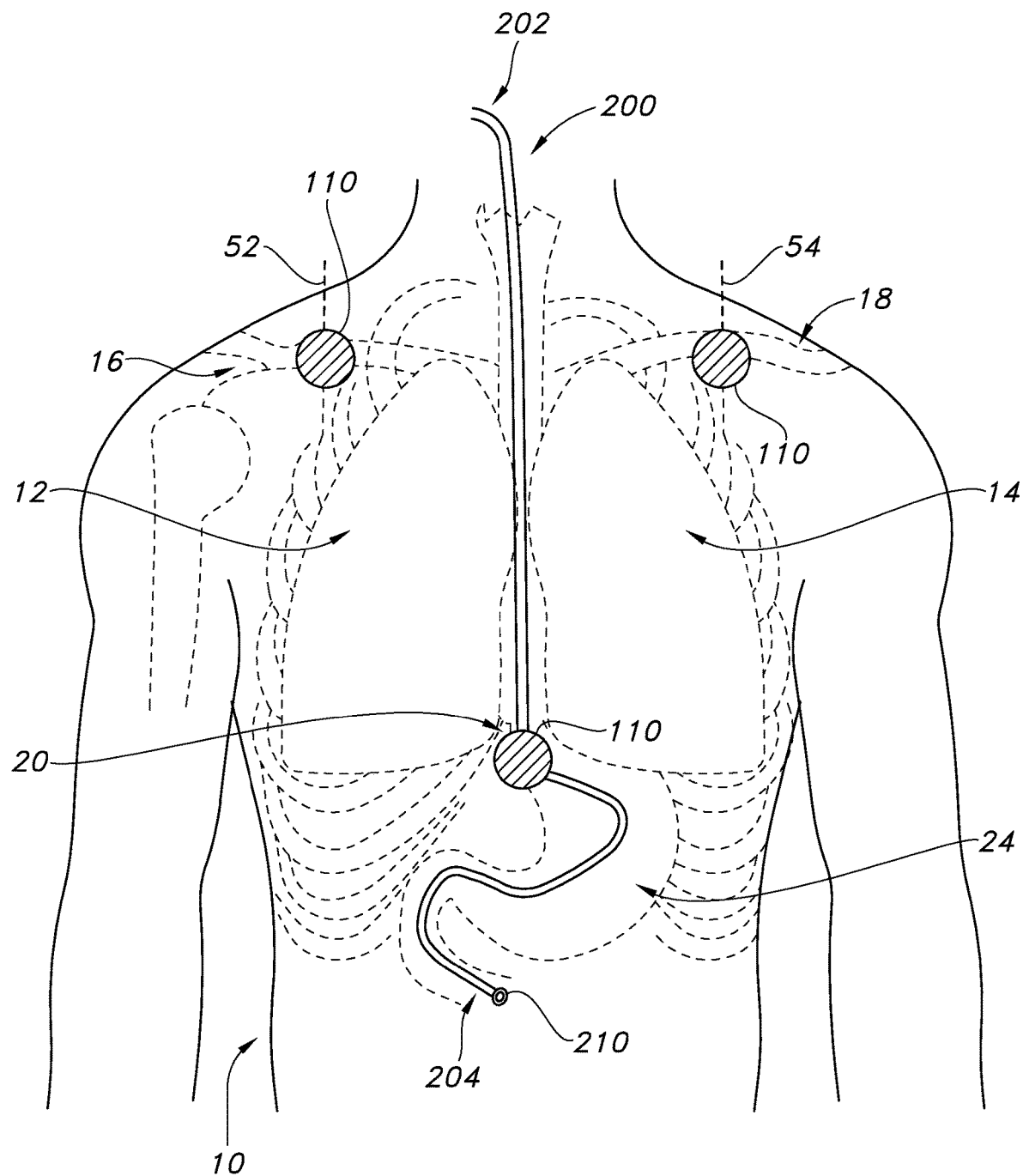
FIG. 2 illustrates a predetermined arrangement of detector devices according to one embodiment of the medical device position guidance system of FIG. 1A.

As shown in FIG. 2, the plurality of external detector devices 110 are configured to be positioned on the external anatomy of a subject 10 in a predetermined arrangement. The predetermined arrangement of the external detector devices 110 can be specific to a particular medical device being positioned in the subject 10. The predetermined arrangement can include multiple predetermined external fixation points on the subject's external anatomy, where each of the predetermined external fixation points are distributed or separated from each other as shown in FIG. 2. The predetermined external fixation points can be based on well-known external anatomical landmarks. In some embodiments, the well-known external anatomical landmarks can be bony landmarks, as the bony landmarks can be located visually or palpated on subjects of any shape or size regardless of physical presentation of the subject, such as the presence of adipose tissue, edema, or other tissues.

Figure 3:
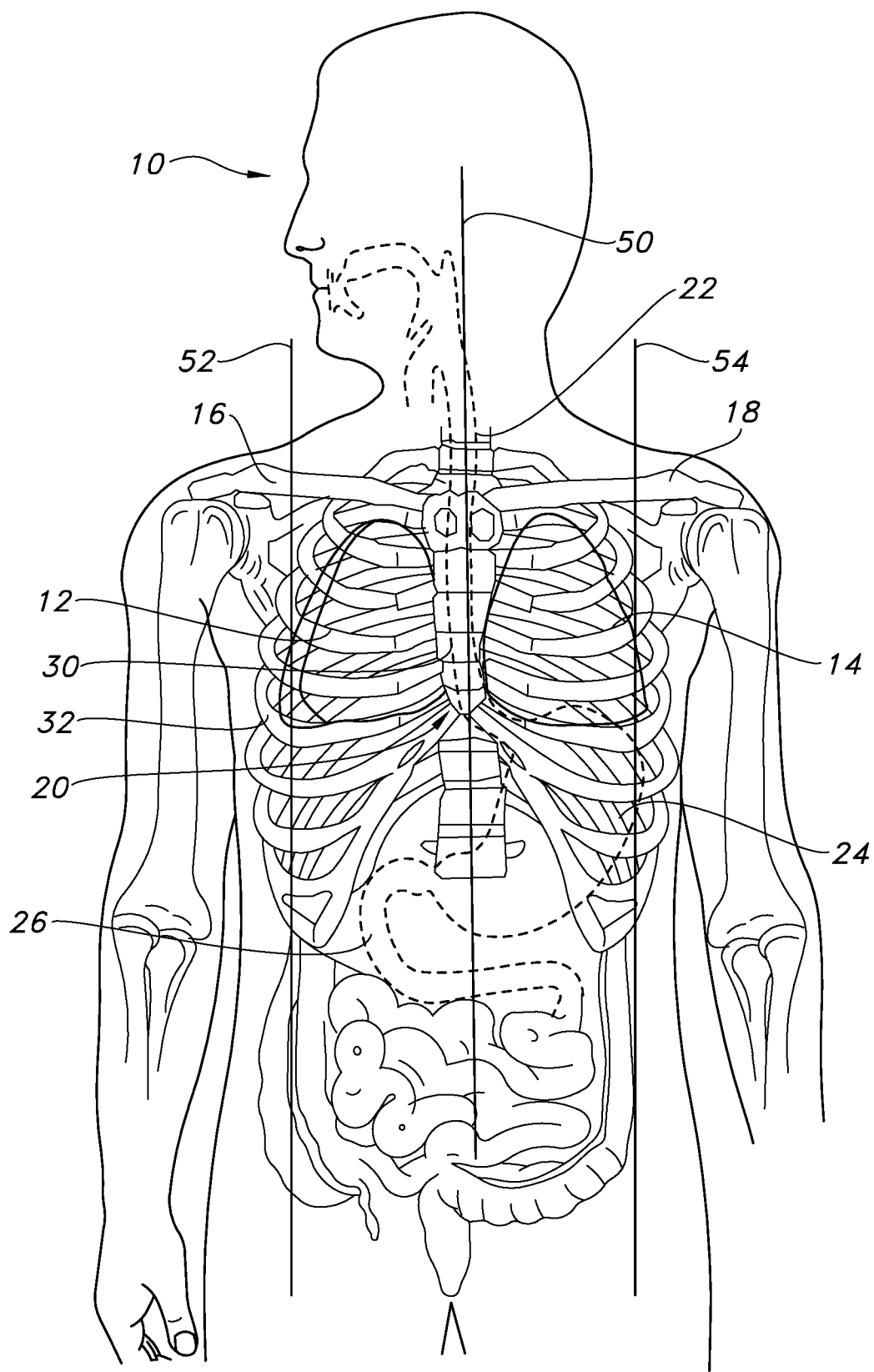
FIG. 3 illustrates anatomical landmarks of a human body.

For example, as illustrated in FIG. 2, when the medical device position guidance system 100 is used to determine a subject's upper anatomy such as for inserting an enteral catheter (feeding tube), three external detector devices 110 can be positioned on the subject 10. For instance, one device 110 can be placed at a right upper landmark, such as the right midclavicular line 52, one device 110 can be placed at a left upper landmark, such as the left midclavicular line 54, and one device 110 can be placed at a central landmark, such as the xiphoid process 20. As illustrated in FIGS. 2 and 3, the xiphoid process 20 is the cartilaginous section at the lower end of the sternum 30 which is generally positioned along the mid-sagittal line 50 and which is not attached to any ribs 32 and is gradually ossified in adult humans. The right and left midclavicular lines 52 and 54 are each imaginary lines which are generally parallel to the mid-sagittal line 50 and pass downwards over the trunk of the human body 10 through the midpoint of the right and left clavicle bones 16 and 18, respectively. However, the midclavicular lines 52 and 54 and the xyphoid process 20 are not the only landmarks that could be used for this purpose. There may be other points of the body to which the predetermined arrangement of the plurality of external detector devices 110 could be reliably co-located or located with a predetermined offset for use in a reliable position guidance system.

Figure 1B:
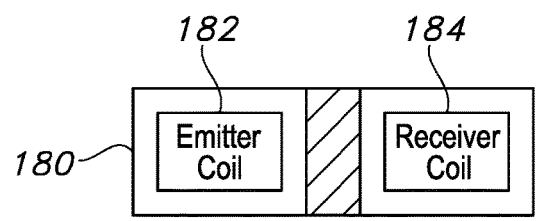
FIG. 1B illustrates an emitter/receiver of the medical device position guidance system of FIG. 1A.
Figure 7:
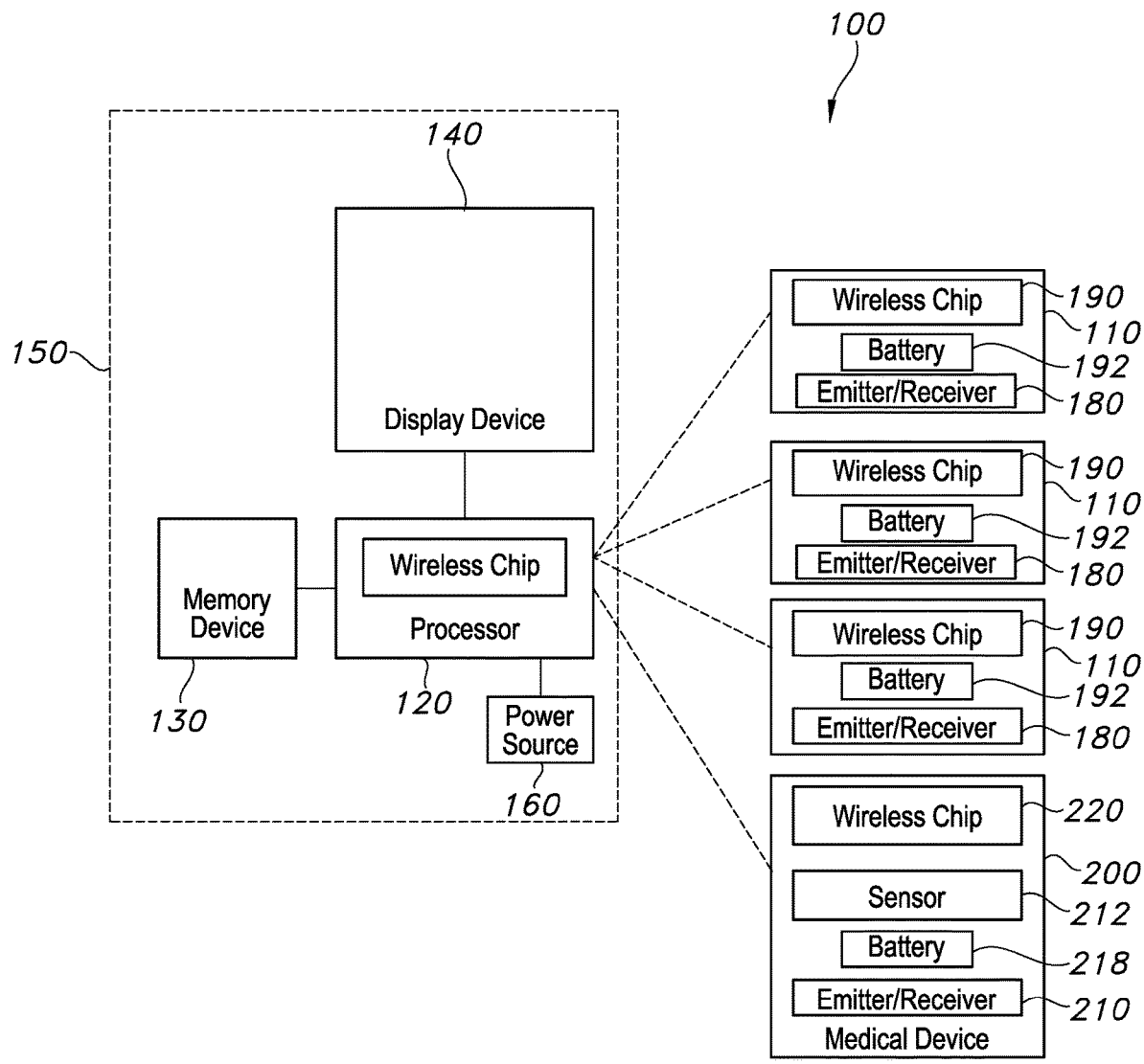
FIG. 7 illustrates a block diagram of a medical device position guidance system according to an alternative embodiment of the present invention.

As illustrated in FIGS. 1A-B and 7, each external detector device 110 includes an electromagnetic emitter and/or receiver 180. In one embodiment, each external detector device may include an electromagnetic emitter 182 formed through a plurality of coils 182 of wire(s) connected to a power source 160. The power source 160 can be a wired or wireless connection to a power source 160 of the apparatus 150 or can be a battery 192 within the external detector device 110. When the power source sends electrical current to the coils 182, the coils 182 can transmit a signal or electromagnetic field capable of being detected by an electromagnetic receiver. Although the coils 182 are disclosed as one example of a magnetic field emitter 182, it should be appreciated that the electromagnetic emitter 182 can include any suitable mechanism or device which generates or produces magnetic energy or a magnetic field, such as a permanent magnet, resistive magnet, or superconducting magnet.

As shown in FIGS. 1A and 7, each external detector device 110 can additionally or alternatively include an electromagnetic receiver 184 that can detect an electromagnetic field or signal generated by an electromagnetic emitter, such as the electromagnetic emitters 182 of the other external detector devices 110. The electromagnetic receivers 184 can each include at least one receiver coil 184, such as three receiver coils 184, that are operable to receive an induced current and detect the induced voltage in response to a magnetic field generated by an electromagnetic field emitter 182 when the magnetic field is directed toward and reaches the receiver coil(s) 182. It should be appreciated that the receiver coils 184 may be any suitable structures capable of receiving an induced current in response to a generated magnetic field. In some embodiments, each of the plurality of external detector devices 110 can include both an electromagnetic emitter 182 and an electromagnetic receiver 184 as part of the emitter/receiver 180. Additionally, there can be shielding 186 within the emitter/receiver 180 between the electromagnetic emitter 182 and the electromagnetic receiver 184. The shielding 186 can prevent signal interference between the electromagnetic emitter 182 and the electromagnetic receiver 184 within the emitter/receiver 180. For example, the shielding 186 can be a barrier between the electromagnetic emitter 182 and the electromagnetic receiver 184 that can be made of conductive or magnetic materials.

In one embodiment, each external detector device 110 can be electrically connected to the apparatus 150 via a wire, cable, or other connection to receive power from the apparatus 150 and to communicate with the processor 120. Alternatively, each external detector device 110 can have a wireless configuration including a battery 192 that provides a voltage to the electromagnetic emitter/receiver 180 and a wireless communication chip 190 configured to communicate with the processor 120. Optionally, the wireless communication chip 190 can include a processor (not shown). The wireless communication chip 190 can be any suitable form of wireless communication capable of sending and receiving digital signals from the processor 120 of the control apparatus 150.

When the plurality of external detector devices 110 are positioned in the predetermined arrangement on the subject 10 based on predetermined external landmarks, the locations of the landmarks can provide adequate separation of the external detector devices 110 on the subject to enable the electromagnetic emitters 182 and receivers 184 of each external detector device 110 to interrogate each other, i.e., for the emitters 182 to emit an electromagnetic field and for the receivers 184 detect the magnetic fields emitted by the respective emitters 182 of the other external detector devices 110. Each external detector device 110 can send one or more signals to the processor 120 detailing the detected coil 184 voltage. Each external detector device 110 can also send one or more signals to the processor 120 detailing the drive signals used to generate the electromagnetic fields with the emitters 182. The processor 120 can compare each of the detected coil voltages and the drive signals used to create the electromagnetic fields to assess and calculate the distance and the relative angular orientation between each of receivers 184 of the external detector devices 110 to define an electromagnetic three-dimensional volume. Using algorithms stored in the memory 130, the processor 120 can use data collected about the electromagnetic three-dimensional volume to derive the subject's external and internal anatomical shape and size within the three-dimensional volume.

For example, as shown in the embodiment illustrated in FIGS. 1A, 2 and 7, the medical device position guidance system 100 can include three external detector devices 110 configured to triangulate and define the subject's upper external anatomy shape and size within the three-dimensional volume. This embodiment including three external detector devices 110 can be beneficial because each of the three external detector devices 110 can form one of three points in space in order to define a single plane, such as an X-Y plane. The determination of an X-Y plane can allow the determination of a distance in the Z-direction. Thus, using three external detector devices 110 can enable the determination of the three-dimensional volume. The three points defined by the three external detector devices 110 can thereby define the patient size and relative anatomical locations within the three-dimensional volume.

The memory 130 can store algorithms defining a generally known pre-defined anthropometric relationship between external anatomy and the internal anatomy, e.g. organs within a subject's body. The processor 120 can execute these algorithms to relate the subject's external anatomy, as detected by the external detector devices 110, to approximate the shape and size of the internal organs associated with that external anatomy. In the embodiment illustrated in FIG. 4, the upper external anatomy shape and size can be used to calculate the shape and size of the lungs, esophagus and stomach. The memory 130 can further store image processing algorithms which the processor 120 can execute in order to visually render a graphical representation of the shapes of the lungs 12 and 14, esophagus 22 and stomach 24 in approximate size and location within the three-dimensional volume and depict the rendered graphical representation of the internal anatomy to scale on a suitable monitor or display 140, e.g. as illustrated in FIG. 2. Thus, the medical device position guidance system 100 can render a graphical representation of the subject's internal anatomy prior to insertion of the invasive medical device 200 to enable the accurate placement of the invasive medical device 200 in the proper location within the body.

The medical device position guidance system 100 can additionally include an invasive medical device 200 having an electromagnetic emitter and/or receiver 210. For example, in the embodiment illustrated in FIG. 6, the invasive medical device can be a catheter 200 that is suitable for enteral nutrition having at least one lumen 208 (passageway extending from proximal to caudal/distal end) or multiple lumens. In one embodiment, the catheter 200 can include markings 205 on the outer wall 206 of the catheter 200 indicating the length of the catheter 200 that has been inserted. An electromagnetic emitter and/or receiver 212 can be located near the tip of the catheter. The electromagnetic emitter and/or receiver 212 can be a coil 212 adjacent to or embedded within the wall 206 of the catheter 200. The electromagnetic emitter and/or receiver 212 is operatively connected to the processor 120, for example, by at least one wire, cable, cord or electrical extension 214, or other wireless connection (not shown). For example, the electromagnetic emitter and/or receiver 212 can connect to a wire or pair of wires 214 which run the length of the catheter 200. In one embodiment, the pair of wires 214 can be incorporated into a metal stylet (not shown) used for inserting the catheter 200 into the subject's gastrointestinal tract. The pair of wires 214 includes at least one signal-carrying wire and can be bound together at the ends of the wires and may be encapsulated in material known to be suitable for its intended use. In a wireless embodiment, the electromagnetic emitter/receiver 212 can connect via wire(s) to a processor of the catheter assembly (not shown), which can then wirelessly receive and/or output information through any suitable wireless communication means 220, such as receiving and/or sending information through an antenna in the form of modulated electromagnetic waves or radio waves to an antenna on the apparatus.

Figure 6:
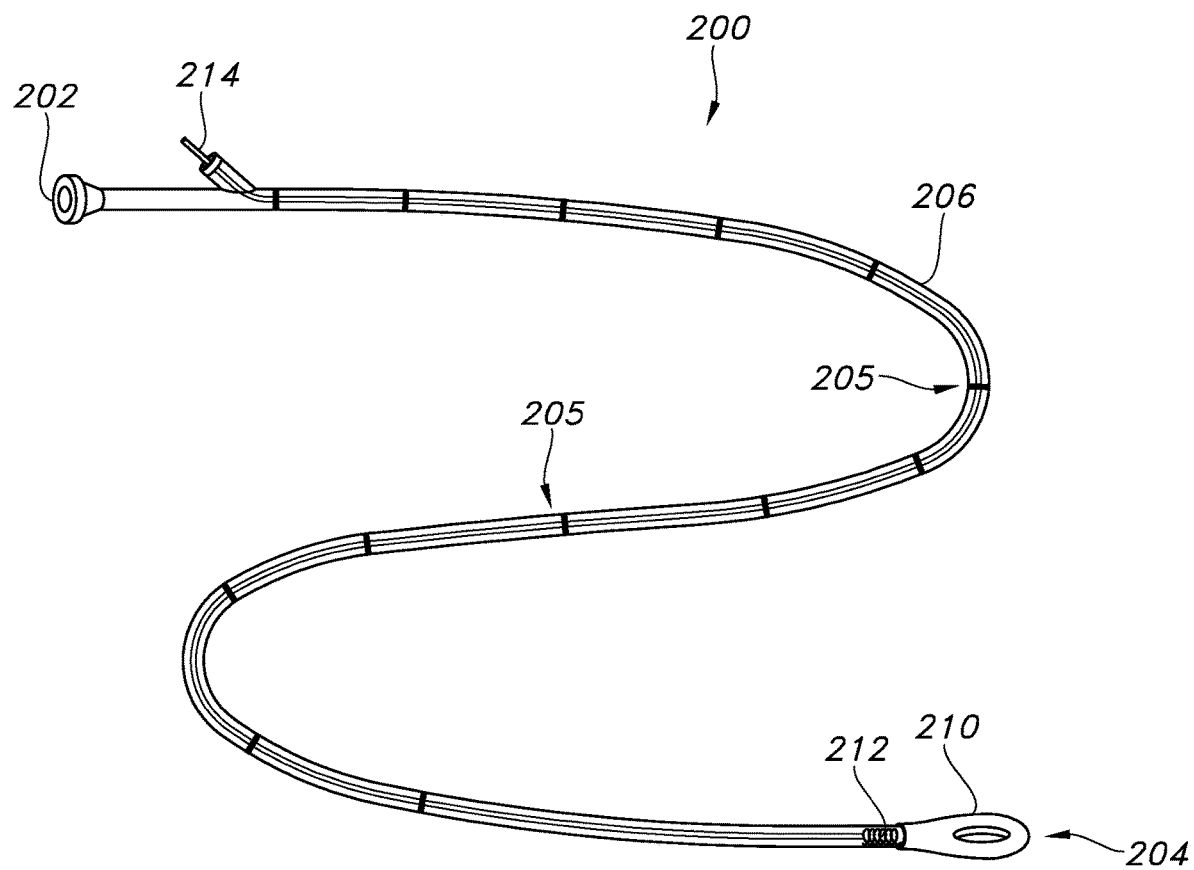
FIG. 6 illustrates an invasive medical device of the medical device position guidance system of FIG. 1A.

As illustrated in FIGS. 1A, 6 and 7, the medical device position guidance system 100 works as follows when positioning an invasive medical device 200. When the distal end 204 of the catheter 200 is inserted into the subject 10, e.g., inserted through the subject's nose or mouth into the gastrointestinal tract, the electromagnetic sensor 212, such as an electromagnetic 212 in the catheter 200 can detect an electromagnetic field generated by each of the emitters 182 of the plurality of external detector devices 110 and/or generate a magnetic field to be detected by each of the receivers 184 of the plurality of external detector devices 110. The magnetic field(s) propagate through the tissue or skin of the subject and induce a voltage in the electromagnetic receiver of the catheter coil 212 or external detector device 110. Information about the induced voltage is then sent to the processor 120 of the apparatus 150. Using the algorithms stored in the memory 120, the processor 120 compares each of the detected coil voltages and the drive signals used to create the electromagnetic fields to determine the relative position and orientation of the catheter tip 210 in relation to each of the external detector devices 110 along the x, y and z axes. Using the information continuously gathered from the plurality of external detector devices 110 to determine the subject's anatomical shape and size along with the relative position and orientation of the catheter tip 210, the relative position and direction of the catheter tip within the subject can be graphically represented on the display. Moreover, the relative position and orientation data of the catheter tip 210 can show the depth of the catheter tip 210 in the z direction within the subject 10.

Using the algorithms stored in the memory 120, the processor 120 can produce indicator data based on the signals received and processed by the processor 120. The processor 120 can also produce indicator data representative of the position of the catheter tip 210 in the form most useful to the user of the apparatus, e.g. a clinician. One such form is a graphical representation of the catheter 200 itself in approximate size and scale relative to the subject's anatomy, e.g. as shown in FIG. 2. To enable the processor 120 to graphically represent the catheter 200, the catheter 200 can send a signal to the processor 120 containing information regarding the size and shape of the catheter 200, or the memory 130 can store information regarding the size and shape of the catheter 200, or a user can input information regarding the size and shape of the catheter into the processor 120. Additionally or alternatively, the processor 120 can produce an indicator image, such as an arrow symbol that is an indication of the position and direction of the coil being detected. The indicator image can be superimposed on the graphical representation of the subject's internal anatomy. For example, when the subject's upper anatomy is graphically represented with images of the lungs 12 and 14, esophagus 22 and stomach 24 in approximate shape and size as described above and as shown in FIGS. 2-3, the catheter tip 210 can be represented with an indicator image, e.g. an arrow, as it is inserted in the subject 10 to view the relative position and direction of the catheter tip 210 within the internal anatomy. The indicator image can be superimposed onto relevant two-dimensional views of the subject's body 10 or a three-dimensional representation of the subject's body 10. For example, the two-dimensional views and/or the three-dimensional representation of the subject's body 10 can be shown in-scale with the size of the subject's body 10, such as being scaled to the actual size of the subject's body 10.

The depth measurements of the catheter tip 210 are a relative measure and not an absolute, but used in the appropriate way can greatly assist trained and experienced personnel in intubating a catheter 200 or other invasive medical device into a patient. The relative depths of the catheter tip 210 are taken of particular note since the ratio of change from person to person will likely be very small. In an example of an enteral feeding catheter intubation, when the catheter tip 210 passes below the xiphoid process 20 it is very deep (e.g., about 17 cm or about 6.5 inches below the plane of the external detector devices 110. While the catheter tip 210 passes through the stomach 24, its tip lies closer and less deep (e.g., about 14 cm or about 5.5 inches) and when passing under the mid-sagittal line 50 it is very shallow and closest to the surface of the subject 10 (e.g., about 8 cm or about 3 inches). In the first part of the duodenum of the small intestine 26 it is relatively shallow (e.g., about 10 cm or about 4 inches) and finally becomes very deep (e.g., about 17 cm or about 6.5 inches) when in the duodenum/jejunum of the small intestine 26. After long term clinical use, an acceptable and reliable range of depths and ratios at the points or regions described (or others) can be developed and used along with the approximate calculations of the subject's internal anatomy shape and size for assisting clinical assessment of the correctness of the route taken by the catheter tip 210. It can be seen that, although not proof of the exact location of the caudal/distal end of the catheter tip 210, the displayed characteristics provide yet another aid to improving clinical decision making with respect to the positioning guidance and location of a catheter.

It should not of course be forgotten that other clinical monitoring techniques may continue to be used thereby increasing the confidence of the clinician that the catheter is appropriately located, whether that be for enteral nutrition or other purposes.

Figure 8:
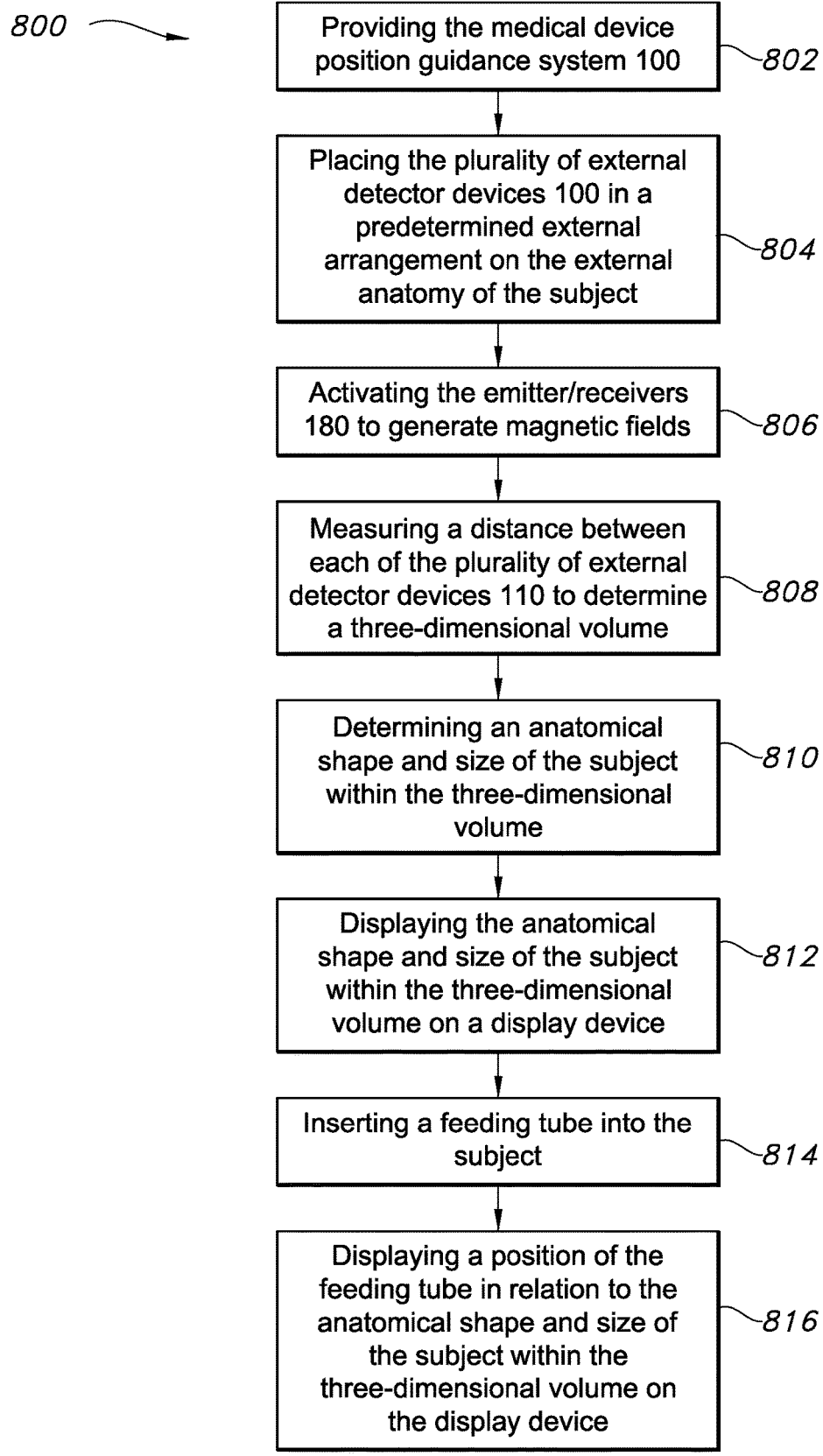
FIG. 8 illustrates a method of determining a size and shape of a subject using the medical device position guidance system of the present invention.

The medical device position guidance system 100 can be used in a method 800 of noninvasively determining a size and shape of a subject 10, as shown in FIG. 8. In step 802, the medical device position guidance system 100 can be provided. For example, a medical device position guidance system 100 can include three external detector devices 110 as described in an embodiment above. In step 804, the plurality of external detector devices can be placed in a predetermined external arrangement on the external anatomy of the subject. The predetermined external arrangement can include a right upper landmark, a left upper landmark and a central landmark.

Then, in step 806, the emitter/receivers 180 of the external detector devices 110 can be activated to begin generating magnetic fields. For example, the processor 120 can send a drive signal to each of the emitter/receivers 180 that causes electric energy to be sent to the electromagnetic emitters 182, thereby causing each of the electromagnetic emitters 182 to generate a magnetic field.

Next, in step 808, a distance between each of the plurality of external detector devices 110 can be measured in order to determine a three-dimensional volume. Particularly, the electromagnetic emitters 182 can emit magnetic fields which induce a current in the electromagnetic receivers 184 of the respective other external detector devices 110. Each emitter/receiver can send one or more signals to the processor 120 detailing the detected coil 184 voltage. Each external detector device 110 can also send one or more signals to the processor 120 detailing the drive signals used to generate the electromagnetic fields with the emitters 182. The processor 120 can compares each of the detected coil voltages and the drive signals used to create the electromagnetic fields to assess and calculate the distance and the relative angular orientation between each of receivers 184 of the external detector devices 110 to define an electromagnetic three-dimensional volume.

In step 810, the defined electromagnetic three-dimensional volume can be used to determine an anatomical shape and size of the subject within the three-dimensional volume. For example, using algorithms stored in the memory 130 including a known pre-defined anthropometric relationship between anatomical landmarks of the predetermined arrangement, the processor 120 can use data collected about the electromagnetic three-dimensional volume to derive the subject's external and internal anatomical shape and size within the three-dimensional volume.

Next, in step 812, the anatomical shape and size of the subject within the three-dimensional volume can be displayed on a display device. For example, the anatomical shape and size of at least one internal organ can be displayed on the display device.

The method 800 can further include a step 814 of inserting a feeding tube 200 into the subject. The feeding tube can include an electromagnetic sensor 212 in an insertion end of the feeding tube 200. Then, in step 816, the system 100 can determine a distance between the electromagnetic sensor and each of the plurality of external detector devices 110. Finally, in step 818, the position of the electromagnetic sensor 212 in relation to the anatomical shape and size of the subject within the three-dimensional volume can be displayed on the display device 140. For example, an indicator image can show the position and/or direction of the electromagnetic sensor 212 of the feeding tube 200 in relation to a two-dimensional or three-dimensional representation of the subject's body. The display can be shown in-scale with the patient's body. Using the indicator image generated in step 218, a user or clinician can adjust the position of the feeding tube 200 until the user or clinician is comfortable with the location of the tip of the feeding tube 200 within the subject.

Although the above embodiments related to positioning an end of a catheter it should be appreciated that the medical device position guidance system is operable to assist in the placement of any medical device or invasive component into a mammal in the course of stent placement, ablation, blockage removal, heat treatment, surgical procedure, fluid delivery or any other suitable invasive procedure. It should be appreciated that any type of catheter may be used for any of the medical procedures described above. It should also be appreciated that any suitable invasive medical device can be used in place of a catheter.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A medical device position guidance system comprising:
a processor;
a plurality of external detector devices configured to be positioned in a predetermined external arrangement on a subject, wherein each detector device is operatively coupled to the processor, further wherein each of the plurality of external detector devices are configured to interrogate each other to determine a distance between each of the plurality of detector devices; and
a memory device storing instructions which when executed by the processor, cause the processor to:
(i) receive signals relating to the distance between each of the plurality of detector devices from each of the plurality of detector devices to determine a three-dimensional volume between the plurality of external detector devices; and
(ii) using the received signals from the plurality of external detector devices and the three-dimensional volume to determine an anatomical shape, size, and/or orientation of the subject within the three-dimensional volume.

2. The medical device position guidance system of claim 1, wherein the plurality of external detector devices comprises a first external detector device, a second external detector device, and a third external detector device.

3. The medical device position guidance system of claim 2, wherein the predetermined external arrangement is based on at least one bony landmark of the subject.

4. The medical device position guidance system of claim 2, wherein the predetermined external arrangement comprises the first external detector device configured to be placed on a right upper landmark of the subject, the second external detector device configured to be placed on a left upper landmark of the subject, and the third external detector device configured to be placed on a central landmark of the subject.

5. The medical device position guidance system of claim 2, wherein the system is configured to maintain a stationary frame of reference relative to the subject.

6. The medical device position guidance system of claim 1, wherein the determined anatomical shape and/or size of the subject is external anatomical shape and/or size of the subject.

7. The medical device position guidance system of claim 6, wherein the memory device further includes information defining a pre-defined anthropometric relationship between the external anatomical shape and size of the subject and the internal anatomical shape and size of the subject, further wherein a display is configured to display the internal anatomical shape and size of the subject within the three-dimensional volume.

8. The medical device position guidance system of claim 7, wherein the internal anatomical shape and size of the subject within the three-dimensional volume includes internal organs within the three-dimensional volume displayed in approximate size and location within the three-dimensional volume.

9. The medical device position guidance system of claim 1, further comprising a medical device configured to be placed within the subject, wherein the medical device includes an electromagnetic sensor configured to be placed within the subject,
wherein the processor is configured to:
(i) determine a distance between the electromagnetic sensor and each of the plurality of external detector devices; and
(ii) cause a display device to display a position of the electromagnetic sensor in relation to the anatomical shape, size, and/or orientation of the subject within the three-dimensional volume.

10. The medical device position guidance system of claim 1, wherein each of the plurality of external detector devices comprises a housing that is configured to be affixed to the subject.

11. The medical device position guidance system of claim 10, wherein the housing of each of the plurality of external detector devices is configured to be adhesively affixed to the subject.

12. The medical device position guidance system of claim 1, wherein each of the plurality of external detector devices further comprises a wireless communication device configured to communicate wirelessly with the processor or a wired connection configured to communicate with the processor.

13. The medical device position guidance system of claim 1, wherein each of the plurality of external detector devices comprises an electromagnetic emitter and/or an electromagnetic receiver.

14. A method of noninvasively determining a size and shape of a subject, the method comprising steps of:
- placing a plurality of external detector devices in a predetermined external arrangement on the external anatomy of the subject, wherein each of the plurality of external detector devices are configured to interrogate each other to determine a distance between each of the plurality of detector devices;
- measuring a distance between each of the plurality of external detector devices to determine a three-dimensional volume; and
- determining an anatomical shape and size of the subject within the three-dimensional volume.

15. The method of claim 14, wherein the plurality of external detector devices includes a first external detector device, a second external detector device, and a third external detector device,
- further wherein the step of measuring includes the first external detector device, the second external detector device, and the third external detector device interrogating each other to triangulate the three-dimensional volume.

16. The method of claim 15, wherein the predetermined external arrangement comprises the first external detector device placed on a central landmark of the subject, the second external detector device placed on a left upper landmark of the subject, and the third external detector device placed on a right upper landmark of the subject.

17. The method of claim 16, wherein the central landmark is the xiphoid process.

18. The method of claim 16, further comprising a step of displaying an anatomical shape and/or size of at least one internal organ in approximate size and location within the three-dimensional volume.

19. The method of claim 14, further comprising steps of:
- inserting a feeding tube into the subject, wherein the feeding tube includes an electromagnetic sensor in an insertion end of the feeding tube;
- determining a distance between the electromagnetic sensor and each of the plurality of external detector devices; and
- displaying a position of the electromagnetic sensor in relation to the anatomical shape and size of the subject within the three-dimensional volume on a display device.

20. The method of claim 14, wherein each of the plurality of external detector devices comprises an electromagnetic emitter and/or an electromagnetic receiver.

* * * * *